(12) United States Patent
Schultz

(10) Patent No.: US 8,123,519 B2
(45) Date of Patent: Feb. 28, 2012

(54) METHOD AND SYSTEM FOR PERSONALIZED ORTHODONTIC TREATMENT

(75) Inventor: Charles J. Schultz, West Babylon, NY (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 11/190,148

(22) Filed: Jul. 26, 2005

(65) Prior Publication Data

US 2006/0093983 A1  May 4, 2006

Related U.S. Application Data

(60) Provisional application No. 60/591,217, filed on Jul. 26, 2004.

(51) Int. Cl.
*A61C 7/08* (2006.01)
*G06G 7/48* (2006.01)

(52) U.S. Cl. ............... 433/6; 433/18; 703/6; 703/11

(58) Field of Classification Search ............. 433/6, 24, 433/7, 18; 128/859–862; 703/6, 11
See application file for complete search history.

(56) References Cited

U.S. PATENT DOCUMENTS

| | | |
|---|---|---|
| 4,755,139 A | 7/1988 | Abbatte et al. |
| 4,793,803 A | 12/1988 | Martz |
| 5,139,419 A | 8/1992 | Andreiko et al. |
| 5,368,478 A | 11/1994 | Andreiko et al. |
| 5,395,238 A | 3/1995 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| 5,464,349 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,533,895 A | 7/1996 | Andreiko et al. |
| 5,683,243 A | 11/1997 | Andreiko et al. |
| 5,692,894 A | 12/1997 | Schwartz et al. |
| 5,829,980 A | 11/1998 | Sheridan et al. |
| 5,975,893 A | 11/1999 | Chishti et al. |
| 6,015,289 A | 1/2000 | Andreiko et al. |
| 6,089,869 A | 7/2000 | Schwartz |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,244,861 B1 | 6/2001 | Andreiko et al. |
| 6,299,440 B1 | 10/2001 | Phan et al. |
| 6,309,215 B1 | 10/2001 | Phan et al. |
| 6,318,994 B1 | 11/2001 | Chishti et al. |
| 6,371,759 B1 | 4/2002 | Schwartz |
| 6,386,864 B1 | 5/2002 | Kuo |
| 6,390,812 B1 | 5/2002 | Chishti et al. |

(Continued)

FOREIGN PATENT DOCUMENTS

EP  0 314 997  5/1989

*Primary Examiner* — Todd Manahan
*Assistant Examiner* — Michael R Ballinger
(74) *Attorney, Agent, or Firm* — Douglas J. Hura; David A. Zdurne; Leana Levin

(57) ABSTRACT

The present invention provides a plastic tray orthodontic device (11) which may have embedded activators (10) and which is provided with an over-shell (12). The over-shell (12) acts as a force module.

17 Claims, 1 Drawing Sheet

U.S. PATENT DOCUMENTS

| | | |
|---|---|---|
| 6,394,801 B2 | 5/2002 | Chishti et al. |
| 6,398,548 B1 | 6/2002 | Muhammad et al. |
| 6,406,292 B1 | 6/2002 | Chishti et al. |
| 6,409,504 B1 | 6/2002 | Jones et al. |
| 6,413,083 B1 | 7/2002 | Hamilton |
| 6,450,807 B1 | 9/2002 | Chishti et al. |
| 6,454,565 B2 | 9/2002 | Phan et al. |
| 6,457,972 B1 | 10/2002 | Chishti et al. |
| 6,463,344 B1 | 10/2002 | Pavloskaia et al. |
| 6,471,511 B1 | 10/2002 | Chishti et al. |
| 6,485,298 B2 | 11/2002 | Chishti et al. |
| 6,488,499 B1 | 12/2002 | Miller |
| 6,499,995 B1 | 12/2002 | Schwartz |
| 6,514,074 B1 | 2/2003 | Chishti et al. |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,602,070 B2 | 8/2003 | Miller et al. |
| 6,602,076 B2 | 8/2003 | Adams |
| 6,607,382 B1 | 8/2003 | Kuo et al. |
| 6,621,491 B1 | 9/2003 | Baumrind et al. |
| 6,626,666 B2 | 9/2003 | Chishti et al. |
| 6,629,840 B2 | 10/2003 | Chishti et al. |
| 6,633,789 B1 | 10/2003 | Nikolskiy et al. |
| 6,665,570 B2 | 12/2003 | Pavloskaia et al. |
| 6,682,346 B2 | 1/2004 | Chishti et al. |
| 6,685,469 B2 | 2/2004 | Chishti et al. |
| 6,685,470 B2 | 2/2004 | Chishti et al. |
| 6,688,886 B2 | 2/2004 | Hughes et al. |
| 6,699,037 B2 | 3/2004 | Chishti et al. |
| 6,705,861 B2 | 3/2004 | Chishti et al. |
| 6,705,863 B2 | 3/2004 | Phan et al. |
| 6,729,876 B2 | 5/2004 | Chishti et al. |
| 7,077,646 B2 * | 7/2006 | Hilliard ............................ 433/6 |
| 2002/0006597 A1 | 1/2002 | Andreiko et al. |
| 2002/0144694 A1 | 10/2002 | Kittelsen et al. |
| 2002/0187451 A1 | 12/2002 | Phan et al. |
| 2002/0192617 A1* | 12/2002 | Phan et al. ....................... 433/6 |
| 2003/0064345 A1 | 4/2003 | Chishti et al. |
| 2003/0190575 A1* | 10/2003 | Hilliard ............................ 433/6 |
| 2003/0224311 A1 | 12/2003 | Cronauer |
| 2004/0110110 A1* | 6/2004 | Chishti et al. ................... 433/24 |
| 2005/0048433 A1 | 3/2005 | Hilliard |
| 2005/0100853 A1* | 5/2005 | Tadros et al. ..................... 433/6 |

* cited by examiner

METHOD AND SYSTEM FOR PERSONALIZED ORTHODONTIC TREATMENT

RELATED APPLICATIONS

This is an ordinary application which claims priority of U.S. provisional patent application Ser. No. 60/591,217 (Case GAC-1977) filed on Jul. 26, 2004.

FIELD OF INVENTION

A system for correcting malocclusions involving CAD/CAM technology, programmed activators, and professional control.

BACKGROUND OF THE INVENTION

The present invention is related to the field of orthodontics and correcting malaligned teeth and arches. "Braces", brackets, bands, tubes, arch wires, and ligatures traditionally have affected these corrections. Implementing the fixed system is uncomfortable for the patient, time consuming for the practice, and unpredictable entailing a high level of "doctor time" to reach the desired result, usually with monthly adjustments over two or more years.

Bonding appliances to the teeth sometimes creates irritation to the soft tissue. Placing appliances is tedious and may affect patient cooperation in the future. Such appliances are also prone to failure during treatment and can extend the time in braces.

Traditional treatment involves a series of visits where wires are changed and adjusted and again take valuable doctor time and immediately after generally cause great discomfort as the wire is tightened.

Orthodontic prescriptions and technology advances have led to about 85% (percent) of the patients being treated using "straight-wire-Type" brackets, mainly in the Roth prescription. There is also a higher torqued system used for extraction cases and a lower torqued for non-extraction cases, with the vast majority of patients worldwide being treated using a few prescriptions. While high technology wires and self-ligating brackets are easing some of the above problems, it still doesn't address others.

In recent years, the amount of adults seeking treatment has grown to the point that it is impacting the profession. While there are near clear ceramic braces for the anteriors, they have their unique treatment challenges and still need the traditional time consuming mechanics. Further, adults generally prefer to have removable appliances for important meetings, occasions, and eating.

In recent years, Align Technologies introduced InvisAlign that has evolved into using high technology systems to create a series of polymeric shells that are activated based on simulation and historic results. Currently, doctors are sent a treatment simulation and must review it and contact the company, sometimes over a period of months, in order for the simulation to be acceptable. The system is time consuming and delays patient treatment. There is again a delay as Align creates a full treatment series trays based on the simulation and ships them for the doctor to check the first model and then set intervals where the progress is monitored. It is not unusual that midcourse corrections are needed again delaying treatment results. The doctor cost for such treatment trays is about 10 times traditional braces and yet their fee cannot be adjusted appropriately. Further, relapse can occur during these delays and the doctor has little control over the treatment progression. Align is also limited as to the types of cases it can treat and disappoints many potential patients.

It is therefore desirable for a simpler, less expensive, more predictable aesthetic removable system for late teen and adult patients.

Tooth positioners and doctor created retainers that are removable and clear have been available for 50 years. InvisAlign has been well marketed for five years to mixed results. Custom designed fixed appliances were discussed in several Sybron/Ormco patents using traditional wires and appliances designed for a specific patient.

SUMMARY OF THE INVENTION

Figure 1:
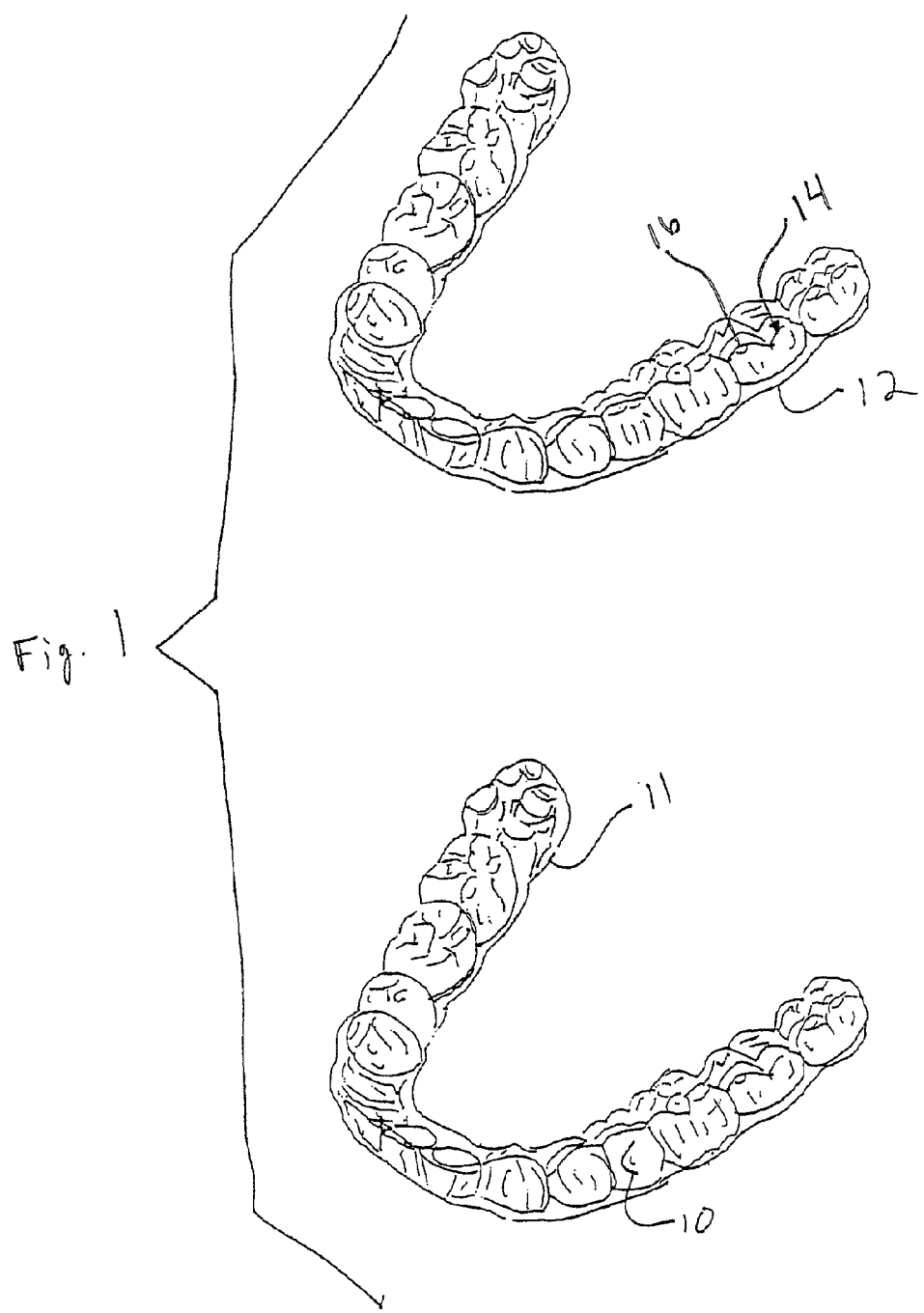
FIG. 1 is an exploded view of a tray system according to the present invention.

According to the present invention, a system for correcting malocclusions using activators embedded in a polymeric or elastic shell and an over-shell in part or whole of the arch designed in the desired end arch form to be the force module is provided. The over-shell shape may be determined through for example, Bolton analysis or digital simulation. The activators need have no arch wire slot, arch wire, or tie wings and are low profile, smooth and virtually invisible in the mouth. The shape or values of the activators are preferably digitally stored in a database to simulate the effect on the teeth in order to select the closest and desired prefabricated activator. The activators are preferably made from a translucent or transparent material that is color stable and follows a proven orthodontic system of programmed activations such as in/out, torque, angulations, and the like; thus avoiding arch wires and ligatures.

There is also provided according to the invention, a system for correcting malocclusions using activators embedded in a material that is translucent or transparent and does not require a series of computer generated trays for treatment but rather the inner tray can be used throughout treatment. This system that the activators are embedded in a tray to fit the malocclusion. The over-tray is in a predetermined, preferably ideal arch form as determined from CAD/CAM technology or resetting the teeth and forming the plastic to the ideal teeth so that it becomes a force module. Activation of the lower force inner shell to correct the malocclusion is provided. Preferably, the over-tray may vary in thickness where bite opening is needed in the posterior and overjet can be monitored via a thinner anterior shell.

According to still another aspect of the invention, a system for correcting malocclusions is provided using activators embedded in a polymeric shell with a synthetic elastic shell or strip attached over said polymeric shell imparting force to the activators thus correcting the malocclusion. The elastic force may be fixed across the entire arch or segment. The elastic force may vary in density or thickness to project varying forces over the inner shell as prescribed by the resistance of the teeth.

A system as above where the inner tray(s) is/are thinner and spring-like while the outer tray(s) issue/issues a force consistent for orthodontic needs.

A system as above where the activators are available in a prefabricated system with a series of related values so that the activators chosen can be identified through simulation on a digital model of the malocclusion or to the doctor's prescription (Rx).

A system for correcting malocclusions using prefabricated activators embedded in polymeric or elastic shells and a series of matching over-shell(s) to effect orthodontic correction where such over-shell(s) may have varying forces. The over-shells and inner shells being able to be placed and removed by quadrant to increase or decrease the force as needed and easier placement by the patient.

The above system where the over-shell(s) may be activated using heated pliers or changes to the ideal design to affect mid course corrections without affecting the inner shell(s). A system as above, used through the bicuspids and while traditional orthodontics can be performed in the posterior molars where it cannot normally be seen by others. A system where a doctor can send a scan of the patient's dentition and bite to a digital laboratory and a 3-D diagnostic model created. The preformed activators values are available in the program and the activators are tested to find the ideal activator for each tooth and then treatment simulated using various outer force shells or strips. Said simulation is sent to the orthodontist for review and either corrections suggested or approved and the digital prescription is then applied in creation of the outer shell. The ideal final arch form is determined by simulation or resetting the teeth and the outer shell or shells created and both the inner and outer shells are marked and sent to the doctor for placement. If needed midcourse corrections can be activated by using adjusting pliers and tools specially made for the task. The doctor therefore is in full control of the treatment progress.

PREFERRED EMBODIMENTS FOR CARRYING OUT THE INVENTION

This invention provides dental professionals with a controlled removable system that uses advanced prefabricated appliances using proven prescriptions to aesthetically and comfortably treat patients. Activators (10), created with the values of the prescription such as the Roth prescription, are embedded in light weight polymeric or elastic inner shells (11) that are designed to be removably fitted and held in outer shells (12) or strips that are removably placed on the teeth with the outer shell or strip as a force module. While outer shell (12) is shown as being a tray in the form of dentition, it will be appreciated that shell (12) can take any form, such as a strip (not shown) as long as it acts to provide orthodontic force, that is, acts as a force module. It is intended that the inner shell is to be used throughout treatment to appreciate ideal tooth movement while the outer shell or strip is changeable due to possible wear in occlusion, discoloration due to hygiene, and to change the force levels as treatment progresses, much as an orthodontist changes arch wires to progressively higher forces as treatment progresses. Also, the thickness of the outer shell or strip can be varied over treatment so that in earlier treatment the posterior can be thicker, opening the posterior bite while the anterior plastic can be thinner to control overjet caused by the plastic arches.

The activators are miniature sized 3-D translucent or transparent geometries that are embedded in the inner shell. Their shape and size are designed to be smooth and comfortable yet to express the torque, angulation, in/out, antirotation, etc. of the proven straight wire type prescriptions, such as the Roth prescription. Since there is no need for tie wings for ligatures, arch wires, or any metal, there is no roughness or sharpness in their wear and the patient and others will hardly notice them at less than a meter away. Both the inner and outer shells would be made of inexpensive material, such as Raintree Essix A+ for the inner shell and C+ for the outer shell. Since the outer shell is always the same dimension, five can be made of each arch at the start of treatment and stored in the patient's records so that it may be immediately changed as needed. Further, the lab with the stored reset model can make force changes immediately so that turnaround time would be days. Should minor activations needed to be added to the outer shell, the doctor can easily apply these in the office-using Hilliard Thermopliers, Hilliard's FITs or Sheridan divots and windows, proven in the professional already. The activators can be formed of color stable plastics such as polyacetyl via injection molding, or with calcium phosphate sintering. Since there is no need to bond the activators, they can be made from a family of color stable ceramics and plastics already proven in dentistry. It is anticipated that no more than three value sets per tooth per activated will need to be stored at the lab and with the ability of instant feedback via systems such as Cadent's OrthoCAD and on-line adjustments and verification, patient starts could be completed in less than a week, at least one fourth of the Align processes time.

It is anticipated that interferes may be present. This is where severely overlapped teeth do not have the room to be pushed into line with the arch. Interproximal stripping may be used or Thermopliers and stripping used to create the space needed. Unlike many Align cases, nothing need be bonded to the teeth to enhance movement as it is all programmed into the activators. Undercuts will retain the shells in place.

A system to hold the inner and outer shells together is anticipated. At the time the outer shell is formed, a retaining device 14 will be formed into the outer shell and a bump to allow easier removal without damaging the shells.

In summary, the preferred process is that the patient meets with the doctor and either a 3-D scan or impression and bite registration is taken. These are sent to a digital diagnostic company such as OrthoCAD, which creates a 3-D digital model of the arches. Information is then used to digitally place the doctor's suggested activators on the model and a simulation movie made of the tooth movement. This downloaded by the doctor, reviewed, improved by the doctor live, and approved. OrthoCAD then sends the digital information to the lab that uses a machine such as a rapid prototype maker to make a real model of the teeth. The activators are selected from inventory and temporarily bonded to the model and a plastic tray is made with the activators imbedded. The tray is trimmed and then the model is reset in ideal occlusion. Several new ideal trays are made and the locking and removal bends 16 placed in the outer shell for holding the inner shell and having finger grips so the patient can more easily remove the tray. The trays are sent to the doctor and treatment begins. If slight modifications are needed, they can be made using existing techniques taught by Dr. Sheridan and Dr. Hilliard. Typically, this system will greatly reduce the amount of interproximal stripping, treatment delays, patient discomfort, and doctor time found with traditional appliances and InvisAlign.

While the above is a complete description of the preferred embodiments of the innovation, various alternatives, modifications, and equivalents may be used. Therefore, the above description should not be taken as limiting the scope of the invention which is defined by the claims.

What is claimed is:

1. A system for correcting malocclusions to an end arch form comprising at least one activator embedded in a polymeric or elastic inner shell and a polymeric or elastic over-shell wherein said over-shell includes a hollow portion and is at least partially in the desired end arch form such that said over-shell acts as a force module and wherein a retaining device is formed into the over-shell to hold the inner shell and over-shell together while allowing separation of the shells without damaging the shells.

2. The system of claim 1, wherein the system is free of arch wires.

3. The system of claim 1, wherein the system is free of metal.

4. A system for correcting malocclusions to an end arch form comprising at least one activator embedded in a polymeric or elastic inner shell and a polymeric or elastic over-shell wherein said over-shell includes a hollow portion and is at least partially in the desired end arch form such that said over-shell acts as a force module and wherein a retaining device is provided having locking and removal bends placed in the over-shell for holding the inner shell and over shell together while allowing separation of the shells without damaging the shells.

5. A system for correcting malocclusions to an end arch form comprising at least one activator embedded in a polymeric or elastic inner shell and a polymeric or elastic over-shell and a database,
   (i) wherein said over-shell includes a hollow portion and is at least partially in the desired end arch form such that said over-shell acts as a force module,
   (ii). wherein activator values are digitally stored in the database to simulate the effect on the teeth in order to select the desired said activator;
   (iii). wherein the over-shell varies in thickness such that an anterior over-shell portion has a smaller thickness relative to a thickness of a posterior over-shell portion; and
   (iv). wherein a retaining device is formed into the over-shell to hold the inner shell and over-shell together while allowing separation of the shells without damaging the shells.

6. The system of claim 5 wherein the at least one activator is made from a translucent or transparent material that is color stable and follows a proven orthodontic system of programmed activations.

7. The system of claim 5, wherein the at least one activator is embedded in a polymeric inner shell with a synthetic elastic over-shell attached over the polymeric inner shell imparting force to the at least one activator for correcting the malocclusion.

8. The system of claim 5, wherein the inner shell is thinner and spring-like while the outer over-shell issues a force consistent for orthodontic needs.

9. The system of claim 5, wherein the at least one activator is selected from a plurality of activators in a prefabricated system of the database, the plurality of activators having a series of related values so that the at least one activator chosen is identified through simulation on a digital model of the malocclusion or to the doctor's prescription (Rx).

10. The system of claim 5, wherein the at least one activator is formed of calcium phosphate or color stable plastics including polyacetyl.

11. A system for correcting malocclusions to an end arch form comprising at least one activator embedded in a polymeric or elastic inner shell and a polymeric or elastic over-shell and a database,
    (i) wherein said over-shell includes a hollow portion and is at least partially in the desired end arch form such that said over-shell acts as a force module,
    (ii) wherein activator values are digitally stored in the database to simulate the effect on the teeth in order to select the desired said activator;
    (iii). wherein the at least one activators is made from a translucent or transparent material that is color stable and follows a proven orthodontic system of programmed activations;
    (iv). wherein a retaining device is formed into the over-shell to hold the inner shell and over-shell together while allowing separation of the shells without damaging the shells; and
    (v). wherein the system is free of arch wires.

12. The system of claim 11, wherein the over-shell varies in thickness such that an anterior over-shell portion has a smaller thickness relative to a thickness of a posterior over-shell portion.

13. The system of claim 11, wherein a thickness of the over-shell is varied over treatment so that in earlier treatment the posterior portion is thicker than the anterior portion.

14. A system for correcting malocclusions to an end arch form comprising at least one activator embedded in a polymeric or elastic inner shell and a polymeric or elastic over-shell and a database,
    (i) wherein said over-shell includes a hollow portion and is at least partially in the desired end arch form such that said over-shell acts as a force module,
    (ii) wherein activator values are digitally stored in the database to simulate the effect on the teeth in order to select the desired said activator,
    (iii). wherein the at least one activator is selected from a plurality of activators in a prefabricated system of the database, the plurality of activators having a series of related values so that the at least one activator chosen is identified through simulation on a digital model of the malocclusion or to the doctor's prescription (Rx);
    (iv). wherein the inner shell is thinner and spring-like while the outer over-shell issues a force consistent for orthodontic needs; and
    (v). wherein a retaining device is provided having locking and removal bends placed in the over-shell for holding the inner shell and over shell together while allowing separation of the shells without damaging the shells.

15. The system of claim 14, wherein:
    (i).
    (ii). the at least one activator is made from a translucent or transparent material that is color stable and follows a proven orthodontic system of programmed activation.

16. The system of claim 14, wherein the over-shells and inner shells being able to be placed and removed by quadrant to increase or decrease the force as needed while providing easier placement by the patient.

17. The system of claim 14, wherein a thickness of at least one of the over-shells is varied over treatment so that in earlier treatment the posterior portion is thicker than the anterior portion.

* * * * *